United States Patent

Reda

[11] 4,343,307
[45] Aug. 10, 1982

[54] FLUSHING NOZZLE AND DILATER FOR COLOSTOMY IRRIGATION

[76] Inventor: Emil T. Reda, 5808 Waycross Rd., Baltimore, Md. 21206

[21] Appl. No.: 216,978

[22] Filed: Dec. 16, 1980

[51] Int. Cl.³ .............................................. A61M 3/00
[52] U.S. Cl. .................................... 128/239; 128/283
[58] Field of Search ............... 128/239, 240, 241, 283, 128/248, 251

[56] References Cited

U.S. PATENT DOCUMENTS

| | | | |
|---|---|---|---|
| 1,237,111 | 8/1917 | Simpson | 128/241 |
| 3,893,446 | 7/1975 | Miller | 128/283 |
| 4,050,461 | 9/1977 | Ruby | 128/283 |
| 4,258,714 | 3/1981 | Leopoldi et al. | 128/239 X |

Primary Examiner—John D. Yasko
Attorney, Agent, or Firm—Schwartz, Jeffery, Schwaab, Mack, Blumenthal & Koch

[57] ABSTRACT

A flushing nozzle and seal for colostomy irrigation, comprising a flushing nozzle having a flushing section at the leading end thereof which can be inserted through a stoma opening, a metering section, and a sealing flange positioned intermediate said flushing and metering sections. The flushing section has a flushing orifice and the metering section has a metering orifice, with the flushing orifice being of relatively larger diameter so as to improve the flushing action. A stoma seal is adapted to fit over the nozzle and has an opening such that the flushing section fits relatively tightly within the opening but permits the stoma seal to be moved longitudinally along the peripheral surface of the flushing section. The stoma seal is generally cup-shaped and includes a leading peripheral edge adapted to contact the abdominal wall around the stoma.

4 Claims, 3 Drawing Figures

FLUSHING NOZZLE AND DILATER FOR COLOSTOMY IRRIGATION

BACKGROUND OF THE INVENTION

The present invention relates as indicated to a flushing nozzle and dilater for colostomy irrigation.

A colostomy is one form of surgical operation that creates an outside opening through the body wall to accommodate body waste. Such opening is referred to as a "stoma", and the stoma is created by extending an unobstructed portion of the colon or ileum through such opening and then stitching the walls of the colon or ileum to the abdominal wall. The type of "ostomy" depends upon the area in the body from which the section has been severed, with a colostomy referring to a surgical operation on the colon or large intestine and resulting in a colostomy stoma. An ileostomy is an operation on the small intestine. Regardless of the type of operation, it will be understood by those in the art that, for one reason or another, a section of the intestinal tract is diverted to an opening through the stoma.

Although a colostomy normally necessarily results in lack of voluntary control over waste discharge, the type of discharge itself depends to a great degree upon the area of the large intestine from which the stoma was diverted. In any event, a stoma bag or disposable pouch is almost inevitably required due to the lack of voluntary control.

Moreover, it is common practice to periodically irrigate the colon through the stoma, for example, once or twice daily, or at other intervals as necessary, with the waste materials as a result of the irrigation also requiring sanitary removal from the area of the stoma. Irrigating fluid normally is directed through the stoma into the colon by means of a syringe or nozzle the removal of which permits the waste products to pass out through the stoma into a collection vessel or the like.

Regardless of the size or location of the stoma and the frequency of irrigation, it is imperative that the stoma be appropriate in size and the appliance consistent in size with the stoma, and that the exposed skin around the stoma be kept as clean as possible. It is also of course important that the appliance used for irrigation purposes provide the maximum cleanliness possible in the discharging process. Thus, it is important that a good seal be maintained between the appliance and the abdominal wall so as to effectively control the waste material and injected water during the drainage process following irrigation. If the nozzle fits tightly within the stoma and the entire region sealed against the abdominal wall, leakage past the nozzle can be minimized or eliminated, thereby avoiding the frequently painful problem where the material being discharged comes into contact with the stoma wall.

Appliances of the general type to which the present invention relates are well known in the art. U.S. Pat. No. 4,004,589 to Neumeier, for example, discloses an ostomy irrigation apparatus having various forms, with each form including a nozzle and a generally conical holder positioned around and extending rearwardly therefrom. A similar appliance is commercially sold by John F. Greer Company, 5335 College Ave., Oakland, Calif. 94618, under the designation "Colostotip". It has been applicant's experience that a conical wall arrangement of this type constitutes substantially to irritability around the stoma thereby making use of such appliance, or appliances comparable thereto having conical wall formation, undesirable.

U.S. Pat. No. 3,292,625 to Marsan discloses an irrigation appliance which includes a relatively unsightly pouch secured to the body of the wearer by means of a belt and extending over the stoma. The appliance is formed with a compressed cellulose sealing means in the form of a sponge through which a catheter tube is inserted for irrigation purposes. The catheter is disposed within a hard plastic sleeve having a radially projecting flange, with the sleeve fitting snugly about the periphery of the catheter. It is stated that the sealing structure provided by the sponge and such sleeve provide assurance against back flow following irrigation.

U.S. Pat. No. 2,865,373 to Recker discloses a colostomy syringe nozzle including an injection tube and a surrounding flange formed of resilient material so as to be deformable around the stoma. In this manner, the flange provides an effective, uniform contact surface with the skin thereby providing a sealing arrangement and also serving to exert a small compressive force on the walls around the stoma so as to better seal the injection tube.

U.S. Pat. No. 1,841,406 to Galazin and U.S. Pat. No. 3,916,896 to Ballard disclose appliances having syringes or nozzles, for use in unrelated environments.

SUMMARY OF THE INVENTION

In accordance with the present invention, a flushing nozzle for irrigation purposes is adapted to extend through the stoma opening, and thus serve as a dilater for such opening. The diameter of the nozzle is based on the average stoma opening diameter, and it will be apparent that nozzle diameters of varying size can be employed depending on the circumstances. The nozzle is formed with a relatively enlarged flushing orifice at its inner end, with the nozzle relatively adjacent its outer end being formed with a more restricted metering orifice. The latter controls the flow of water from the irrigating bag, and the relatively large flushing orifice prevents jetting of the water and thus provides better flushing action.

A stoma seal, generally cup-shaped in form, is formed with a central opening through which the nozzle extends, with relatively close tolerance. Such tolerance provides a rather tight fit between the nozzle and the opening provided therefor in the stoma seal thereby serving to inhibit liquid flow between the opening and the orifice. The stoma seal is sufficiently large in diameter to circumscribe the stoma and engage at its inner peripheral edge the abdominal wall around the stoma thereby sealing off any liquid which might otherwise travel radially outwardly after passing between the stoma and the nozzle. Both the stoma seal and nozzle are preferably formed of a relatively soft yet rigid plastic material, for example, Teflon, so as to minimize the friction and consequent irritation both at the stoma opening through which the nozzle extends and the abdominal wall area with which the inner periphery of the stoma seal contacts.

A further feature of the invention is the provision of a radially enlarged flange approximately intermediate the length of the nozzle, with the inner surface of the flange being planar and engaging the outer planar surface of the stoma seal to provide a second area of sealing. Any leakage past the first sealing area between the periphery of the nozzle and the opening in the stoma seal thus encounters the sealing flange to serve as a further inhibition to leakage. The flange is integrally formed with the nozzle, and the area of the nozzle immediately behind such flange permits the nozzle to be gripped and easily inserted through the stoma.

The outer end of the nozzle is serrated or grooved so as to provide a surface adapted to receive a standard hose connection to any standard enema or irrigation bag hose by means of which the flushing is effected.

These and other objects of the invention will become apparent as the following description proceeds with particular reference to the application drawing.

BRIEF DESCRIPTION OF THE APPLICATION DRAWING

DETAILED DESCRIPTION OF THE PREFERRED EMBODIMENTS

Figure 1:
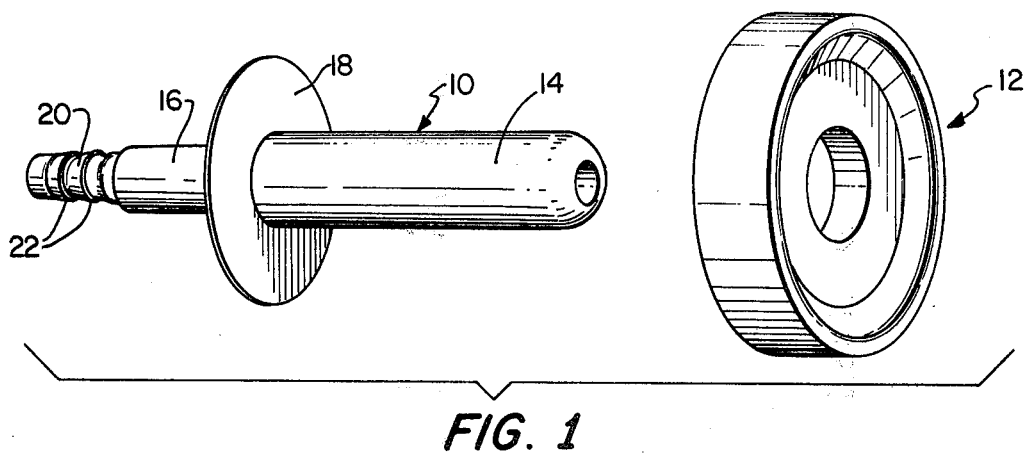
FIG. 1 is a perspective, exploded view showing the nozzle and stoma seal in spaced relation.
Figure 2:
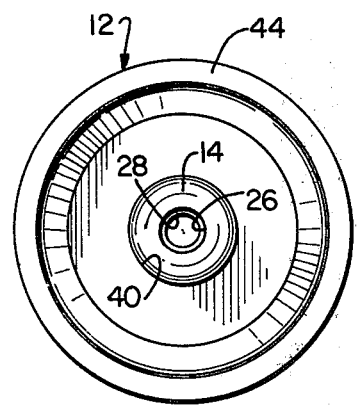
FIG. 2 is a top plan view showing the stoma seal and the nozzle positioned through the central opening formed in the seal.
Figure 3:
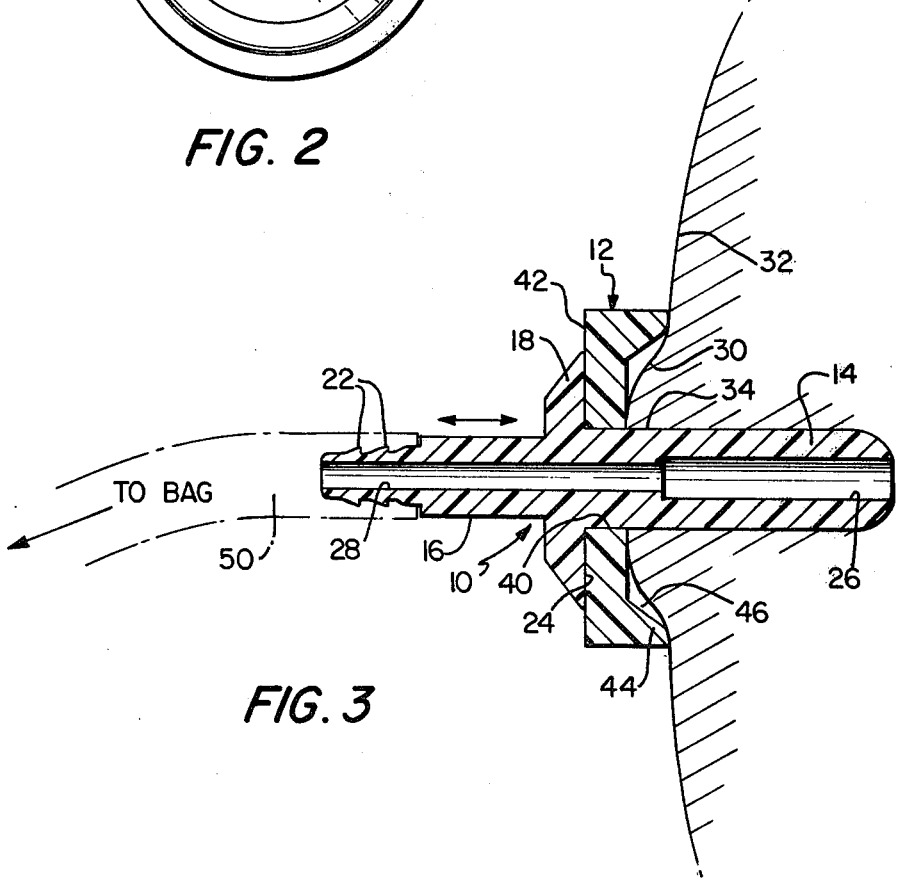
FIG. 3 is a vertical cross-sectional view showing the nozzle and seal in operative position, with the nozzle extending through the stoma so as to condition the entire assembly for irrigation.

Referring now to the application drawing, wherein like parts are indicated by like reference numerals, the flushing nozzle in accordance with the present invention is generally indicated at 10, and the stoma seal is generally indicated at 12. The nozzle includes a relatively enlarged flushing section 14 and a metering section 16, with a sealing flange 18 being formed between such sections. As shown in FIG. 3, the sealing flange is preferably integrally formed with the nozzle, with the latter being preferably made of a non-abrasive but yet rigid material. Experiences have shown that Teflon is very satisfactory and meets those characteristics. The nozzle is formed with a further reduced section 20 at the outer end thereof, with the section 20 being formed with a series of projections commonly designated at 22 to adapt such section to receive the hose of a standard enema or irrigation bag, with the hose to such bag being shown in dashed lines in FIG. 3. As shown in the same figure, the leading face 24 of the sealing flange 18 is planar to provide a sealing surface as will be presently described.

The flushing section 14 of the nozzle is formed with a flushing orifice 26 which extends throughout the flushing section, terminating prior to the sealing flange 18, with the metering section 20 being formed with a metering orifice 28 smaller in cross-sectional diameter than the flushing orifice 26. It will be understood that the metering orifice controls the flow of water from the irrigating bag, with the much larger flushing orifice preventing jetting of the water and providing a uniform and non-turbulent flow so as to provide better flushing action. It will be noted in this regard that the size of the metering orifice 28 is to a large extent controlled by the necessity to provide the serrated end section 22 to adapt the appliance to use with normal irrigation bags. It has been my experience that when the metering orifice is so restricted, an uncomfortable and high jetting action results. The enlarged orifice 26 prevents this.

The stoma 30 connected to the abdominal wall 32 is formed with a stoma opening 34 in the normal manner. As understood by those in the art, the opening is normally more restricted in size than the diameter of the flushing section 14 of the nozzle whereby the opening is dilated as the nozzle is pushed therethrough. During penetration of the nozzle through the stoma opening, the nozzle can be conveniently gripped by the metering section 16, with the fingers engaging the rear faces of the sealing flange 18.

The stoma seal 12 is formed with a central opening 40 comparable but slightly greater in diameter than the outside diameter of the flushing section 14 of the nozzle. This close tolerance permits the flushing section to be pushed through the stoma seal but yet provides a relatively tight seal at the interface between those members. Leakage along such interface is thereby inhibited to the extent possible. The seal further includes a rear planar surface 42 against which the front planar surface 24 of the flange 18 is adapted to contact, and a peripheral sealing portion 44 which is substantially axially offset from a vertical plane through the stoma seal, with the leading edge of the peripheral sealing portion 44 engaging the abdominal wall 32 around the stoma 30. The seal provided by the sealing portion 44 thus inhibits leakage from the interface between the stoma opening and the outer periphery of the flushing section radially outwardly into the opening 46 provided in the stoma seal. As above noted, the seal 12 is also preferably formed of a non-abrasive plastic material whereby contact of the peripheral sealing portion 44 thereof with the abdominal cavity does not result in irritation of the abdominal wall around the stoma.

In the use of the device, the stoma seal 12 is positioned over the flushing section 14 of the nozzle, in the orientation thereof shown in FIG. 3. The seal 12 is moved rearwardly until the rear planar face 42 engages the contiguous planar face 24 of the sealing flange 18. The nozzle, with seal 12 attached as described, is then positioned at the stoma opening, with the flushing section 14 being pushed through and dilating the stoma opening. The penetration in the form shown is limited by the contact of the sealing flange 18 with the stoma seal at the contiguous planar faces thereof, and the consequent engagement of the peripheral sealing portion 44 of the stoma seal with the abdominal wall around the stoma. The hose connection, shown in dashed lines at 50, is then positioned and retained around the end of the metering section to condition the assembly for irrigation. Water is then introduced into the assembly through the hose connection, with the water first passing through the relatively reduced diameter metering orifice 28 and thereafter into the enlarged flushing orifice 26. Due to the enlarged flushing orifice, a better flushing action is provided, and the amount of water will of course depend on the area of the intestine from which the stoma has been formed. To flush the irrigation, the connecting hose is associated with a conventional discharge receptacle or the like which forms no part of the present invention.

It will be seen that the invention provides substantially improved sealing action. Any discharge seeping through the stoma opening around the flushing section 14 of the nozzle is retained within the stoma seal by virtue of the peripheral sealing portion 44 of the seal. In the event leakage occurs through the area between the periphery of the flushing nozzle and the seal opening 40, which is of close tolerance as above noted, a second sealing action is afforded by virtue of the sealing flange 18, which inhibits any leakage from flowing radially along the interface between the planar surfaces 24 and 42 of the seals 18 and 12, respectively. Thus, an improved sealing arrangement is provided.

At the sacrifice of sealing effectiveness, modifications can be made from the invention as above described. For example, the nozzle need not be inserted to the extend shown in FIG. 3. Only partial insertion is adequate in many instances, with the user being able to tell quite readily the appropriate degree of penetration of the nozzle through the stoma opening. In the event the penetration is less than that shown in FIG. 3, the flange 18 will of course be spaced from the stoma seal 12, and the further sealing effect between the flange and the rear face 42 of the stoma seal will not be available. However, the flange is such instance can be used more or less as a gauge to determine penetration, and a forefinger, for example, can be inserted between the adjacent face of the stoma seal and the flange 18 to provide the desired length of penetration. The flange 18 is also very useful in manipulating the nozzle.

A further possible modification would be the forming of the stoma seal 12 integral with the nozzle. The obvious disadvantage of that arrangement is that the penetration of the nozzle is fixed by virtue of the necessity of the leading edge of the stoma seal being applied in sealing contact against the abdominal wall. The obvious advantage of an integral flange construction would be to reduce the potential of leakage through the seal, and the possible reduced costs of manufacture. It will be understood that the depth of the seal, that is, the distance of the stoma seal in an axial direction, can be widely varied so as to accommodate stomas of varying size.

In either of the described modifications, the enlarged flushing orifice 26 would be maintained to provide the advantages above described.

I claim:

1. A flushing nozzle and seal for colostomy irrigation, comprising:
   (a) a flushing nozzle having a flushing section at the leading end thereof which can be inserted through a stoma opening, a metering section, and a sealing flange integrally formed with said nozzle and positioned intermediate said flushing and metering sections, the outer end of said metering section being adapted to receive a connecting hose to an irrigation source, said flushing section having a flushing orifice and said metering section having a metering orifice, said orifices being coaxial and longitudinally spaced, with said flushing orifice being of relatively larger diameter so as to improve the flushing action, and
   (b) a stoma seal adapted to fit over said flushing section and having an opening such that said flushing section fits relatively tightly within said opening but permits said stoma seal to be moved longitudinally along the peripheral surface of said flushing section, said stoma seal being generally cup-shaped and including a leading peripheral edge adapted to contact the abdominal wall around the stoma, and a rear surface against which the leading end of said sealing flange can selectively engage,
   whereby sealing is provided at least at the peripheral edge of said stoma seal and the interface of said flushing section and the opening in said stoma seal.

2. The combination of claim 1 wherein the leading face of said sealing flange and the rear surface of said stoma seal are planar so as to provide solid face-to-face contact when said nozzle is selectively moved inwardly so as to contact said stoma steal.

3. The combination of claims 1 or 2 wherein said nozzle and said stoma seal are made of a non-abrasive yet rigid plastic material.

4. The combination of claim 3 wherein said plastic material is Teflon.

* * * * *